(12) United States Patent
Wachtel et al.

(10) Patent No.: US 8,919,342 B2
(45) Date of Patent: Dec. 30, 2014

(54) INHALER

(75) Inventors: Herbert Wachtel, Ingelheim am Rhein (DE); Matthew Neil Sarkar, Cambridge (GB); Ivan Milivojevic, Cambridge (GB); Quentin Harmer, Waterbeach (GB)

(73) Assignees: Boehringer Ingelheim International GmbH, Ingelheim am Rhein (DE); Vectura Delivery Devices Limited, Chippenham (GB)

( * ) Notice: Subject to any disclaimer, the term of this patent is extended or adjusted under 35 U.S.C. 154(b) by 1052 days.

(21) Appl. No.: 12/671,115

(22) PCT Filed: Jul. 31, 2008

(86) PCT No.: PCT/EP2008/060078
§ 371 (c)(1),
(2), (4) Date: Jun. 28, 2010

(87) PCT Pub. No.: WO2009/016238
PCT Pub. Date: Feb. 5, 2009

(65) Prior Publication Data
US 2010/0313886 A1   Dec. 16, 2010

(30) Foreign Application Priority Data
Aug. 1, 2007   (EP) .................................. 07113624

(51) Int. Cl.
*A61M 15/00* (2006.01)
*B65D 83/06* (2006.01)

(52) U.S. Cl.
CPC ......... *A61M 15/0028* (2013.01); *A61M 15/003* (2013.01); *A61M 15/0033* (2013.01); *A61M 2202/064* (2013.01); *A61M 2206/16* (2013.01)
USPC ............. 128/203.21; 128/203.12; 128/203.15

(58) Field of Classification Search
CPC ................. A61M 13/00; A61M 15/00; A61M 2015/0035; A61M 15/06; A61M 2015/0041; A61M 2206/16; A61M 15/0045; A61M 2015/0033; A61M 2202/064

USPC ............. 128/203.12, 203.14, 203.15, 203.19, 128/203.21, 203.27; 604/57–58
See application file for complete search history.

(56) References Cited

U.S. PATENT DOCUMENTS

| 3,807,400 A | 4/1974 | Cocozza |
| 3,906,950 A | 9/1975 | Cocozza |

(Continued)

FOREIGN PATENT DOCUMENTS

| CA | 2497059 | 8/2003 |
| CN | 1437551 A | 8/2003 |

(Continued)

OTHER PUBLICATIONS

Office Action, and English translation, dated Oct. 23, 2012, issued by the Japanese Patent Office in connection with corresponding Japanese Application No. 2010-518680.

(Continued)

*Primary Examiner* — Justine Yu
*Assistant Examiner* — Douglas Sul
(74) *Attorney, Agent, or Firm* — Davidson, Davidson & Kappel, LLC

(57) ABSTRACT

In an inhaler for administering a powdery medicament in the form of an inhalable substance, substance formulation or mixture, a blister cavity to be opened by piercing elements (11) is mounted in the lower part (1) of a housing (2), which has an upper part (6), designed as mouthpiece and with an inhalation channel (16), and of the lower part (1), which has an air inlet opening (9). The inhalation channel (16) of the upper part (6) of the housing has a unit (15) for dispersing the powdery medicament, said unit (15) being connected to the piercing elements (11), wherein the upper part (6) of the housing can be moved relative to the lower part (1) of the housing in order to open the blister cavity.

52 Claims, 6 Drawing Sheets

(56) References Cited

U.S. PATENT DOCUMENTS

Figure 1:
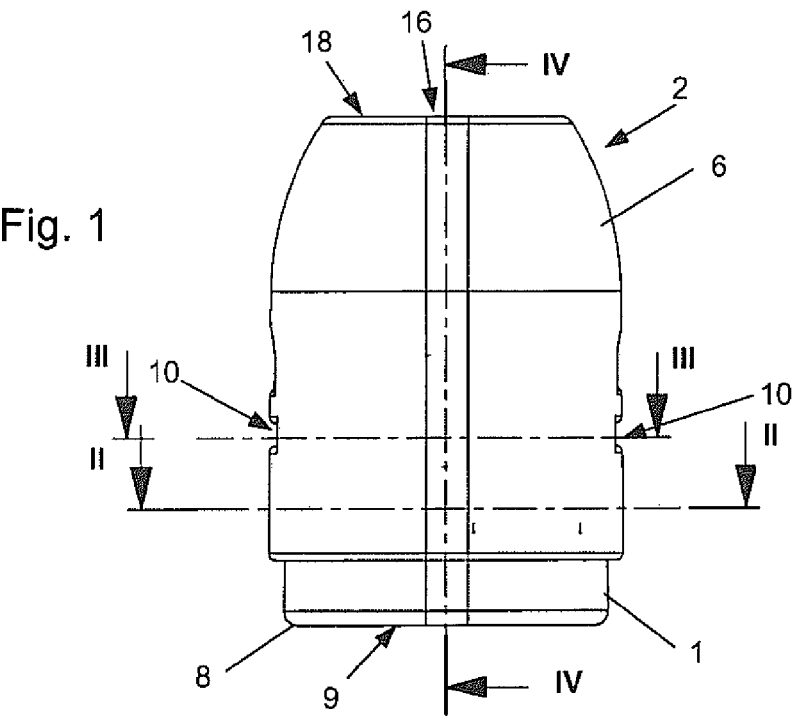
Figure 2:
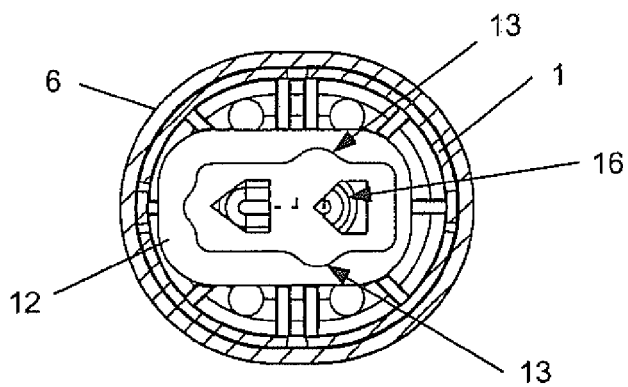
Figure 3:
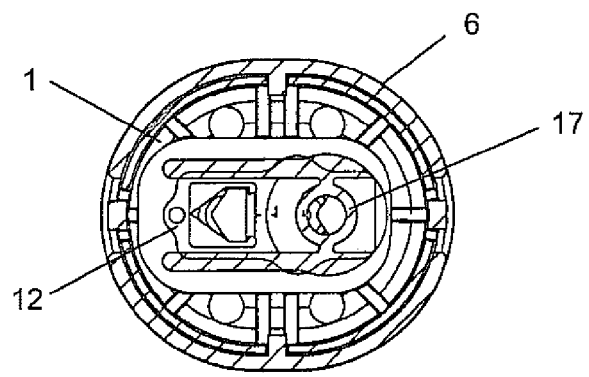
Figure 4:
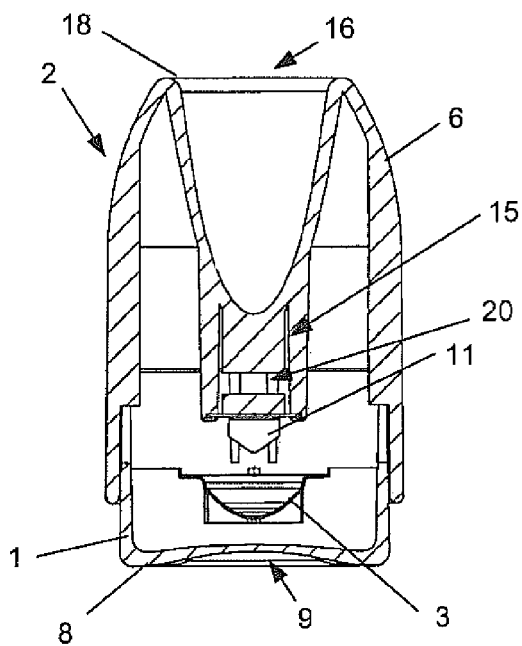
Figure 5:
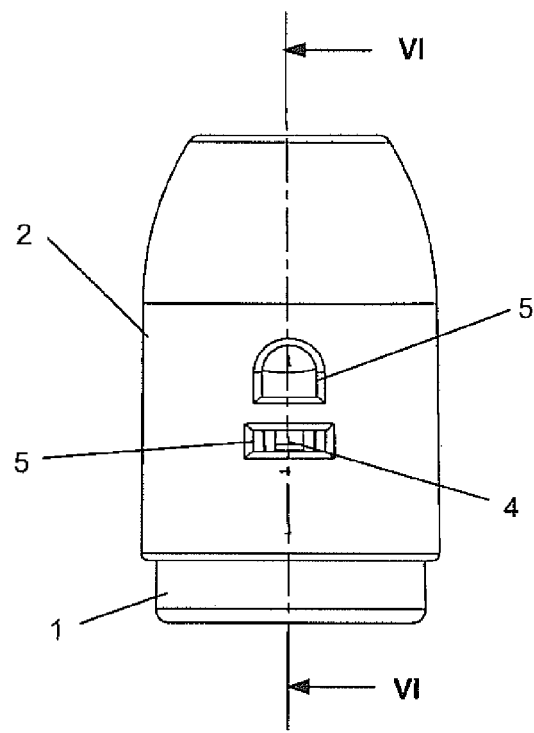
Figure 6:
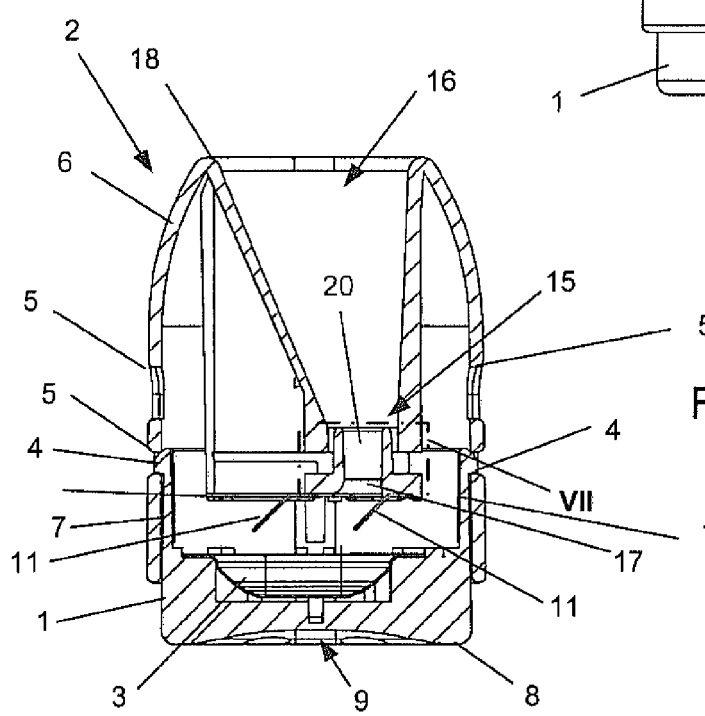

| | | | |
|---|---|---|---|
| 4,210,140 A | 7/1980 | James et al. | |
| 4,338,931 A * | 7/1982 | Cavazza | 128/203.15 |
| 4,423,724 A | 1/1984 | Young | |
| 5,070,870 A | 12/1991 | Pearce | |
| 5,301,666 A | 4/1994 | Lerk et al. | |
| 5,476,093 A | 12/1995 | Lankinen | |
| 5,533,505 A | 7/1996 | Kallstrand et al. | |
| 5,676,130 A | 10/1997 | Gupte et al. | |
| 5,740,794 A * | 4/1998 | Smith et al. | 128/203.15 |
| 5,881,719 A | 3/1999 | Gottenauer et al. | |
| 6,273,086 B1 * | 8/2001 | Ohki et al. | 128/203.21 |
| 6,347,629 B1 | 2/2002 | Braithwaite | |
| 6,367,473 B1 | 4/2002 | Kafer | |
| 7,225,808 B2 * | 6/2007 | Davies et al. | 128/203.15 |
| 7,258,119 B2 * | 8/2007 | Mazzoni | 128/203.21 |
| 7,814,905 B2 | 10/2010 | Schuler et al. | |
| 7,832,399 B2 * | 11/2010 | Ganem et al. | 128/203.21 |
| 8,181,647 B2 | 5/2012 | Ishizeki et al. | |
| 2001/0029947 A1 * | 10/2001 | Paboojian et al. | 128/203.15 |
| 2002/0088463 A1 | 7/2002 | Keanet et al. | |
| 2003/0053960 A1 | 3/2003 | Heijerman et al. | |
| 2003/0140923 A1 * | 7/2003 | Taylor et al. | 128/203.12 |
| 2003/0188747 A1 | 10/2003 | Ohki et al. | |
| 2004/0149283 A1 * | 8/2004 | Hochrainer | 128/203.15 |
| 2006/0147389 A1 | 7/2006 | Staniforth et al. | |
| 2006/0185672 A1 | 8/2006 | Pinon et al. | |
| 2006/0254583 A1 * | 11/2006 | Deboeck et al. | 128/203.15 |
| 2007/0107722 A1 | 5/2007 | Hoelz et al. | |
| 2007/0125375 A1 | 6/2007 | Finlay et al. | |
| 2007/0137645 A1 | 6/2007 | Eason et al. | |
| 2007/0295332 A1 | 12/2007 | Ziegler et al. | |
| 2008/0314384 A1 | 12/2008 | Harris et al. | |
| 2010/0000529 A1 | 1/2010 | Prime et al. | |
| 2011/0120463 A1 * | 5/2011 | Esteve et al. | 128/203.15 |

FOREIGN PATENT DOCUMENTS

| | | |
|---|---|---|
| CN | 1678406 A | 10/2005 |
| CN | 1867369 A | 11/2006 |
| DE | 69319100 | 1/1999 |
| DE | 10239443 | 3/2004 |
| EP | 0041783 | 12/1981 |
| EP | 0547429 B1 | 6/1996 |
| EP | 0911047 | 4/1999 |
| EP | 0835148 | 9/2001 |
| EP | 1129705 | 11/2001 |
| EP | 1760008 | 3/2007 |
| EP | 1649886 B1 | 4/2008 |
| FR | 2224175 | 10/2006 |
| GB | 2407042 B | 10/2007 |
| JP | A 1975048782 | 5/1975 |
| JP | 53100695 A | 9/1978 |
| JP | B 1990023192 | 5/1990 |
| JP | H07501231 A | 2/1995 |
| JP | A 1996500743 | 1/1996 |
| JP | 2000-504248 A | 4/2000 |
| JP | 2001-070403 A | 3/2001 |
| JP | 2003-535656 A | 12/2003 |
| JP | 2004-529664 A | 9/2004 |
| JP | 2004-530498 A | 10/2004 |
| JP | 2005-506855 A | 3/2005 |
| JP | 2006-502759 | 1/2006 |
| JP | 2006-507876 A | 3/2006 |
| TW | 200613021 A | 5/1994 |
| WO | WO89/07464 A1 | 8/1989 |
| WO | WO9300951 A1 | 1/1993 |
| WO | WO93/18811 A1 | 9/1993 |
| WO | WO97/27892 A1 | 8/1997 |
| WO | WO01/07107 A2 | 2/2001 |
| WO | WO01/98174 A1 | 12/2001 |
| WO | WO02/00280 A2 | 1/2002 |
| WO | WO02/089880 A2 | 11/2002 |
| WO | WO03/000325 A1 | 1/2003 |
| WO | WO2004/050152 A1 | 6/2004 |
| WO | WO 2005025656 A1 * | 3/2005 |
| WO | WO2005037353 A1 | 4/2005 |
| WO | WO 2006/026237 | 3/2006 |
| WO | WO2006/066908 A1 | 6/2006 |
| WO | WO 2006/108877 | 10/2006 |
| WO | WO 2006108877 A2 * | 10/2006 |
| WO | 2007-014744 A | 1/2007 |
| WO | 2007-533363 A | 11/2007 |
| WO | WO2008/051621 A2 | 5/2008 |

OTHER PUBLICATIONS

International Search Report in connection with International Application No. WO2009/016238 (Patent No. PCT/EP2008/060078) issued Feb. 9, 2009.

Office Action, and English translation, dated Jan. 2, 2014, issued by the Taiwanese Patent Office in connection with corresponding Taiwanese Application No. 12/671,115.

* cited by examiner

INHALER

This application is a U.S. national phase application under U.S.C. §371 of International Application No. PCT/EP2008/060078, filed Jul. 31, 2008, which claims priority to European Patent Application No. EP07113624.6, filed Aug. 1, 2007, the disclosures of which are hereby incorporated by reference in their entirety.

FIELD OF THE INVENTION

The invention relates to an inhaler for administration of a pulverulent medicament in the form of an inhalable substance, substance formulation or substance mixture from a blister cavity which is to be opened by piercing elements and is mounted in a lower housing part of a housing which is composed of an upper housing part, which is in the form of a mouthpiece and has an inhalation channel, and a lower housing part, which has an air inlet opening.

BACKGROUND

EP 0 911 047 A1 discloses an inhaler for the inhalation of pulverulent medicaments from capsules, which inhaler comprises a lower part having two windows and a plate in which there are capsule holders and air inlet openings. An inhalation chamber is further connected to the plate, at which there is provided a head which is equipped with two ground needles and is movable against a spring. A mouth tube is connected to an upper part of the inhaler, and a lid is connected in a hinged manner to the lower part, to the plate and to the upper part. This inhaler has a complex construction and is intended for multiple use.

EP 0 835 148 B1 further describes an inhaler for the administration of medicaments from a strip-shaped blister pack, a blister cavity being emptied by means of a pressing aid. The inhaler substantially comprises an elongate housing consisting of at least two housing parts which are pivotably connected to one another by way of a hinge. A recess as a bearing for receiving the blister strip is formed in one of the housing parts. The housing has a mouthpiece on one narrow side and, on the narrow side opposite the mouthpiece, it has an air inlet opening which is connected to the mouthpiece by way of an air channel. The air channel is designed to receive the medicament from the blister cavity, the medicament being released by a pressing-out plunger associated with the housing, the pressing-out plunger, when pressed by the user of the inhaler, causing the cover film of the blister cavity to be torn open, whereupon the medicament either remains in the cavity of the blister or falls into a powder channel of the air channel. This inhaler is intended for multiple use owing to its construction.

In order to inhale the medicament effectively, the patient must bring the mouthpiece of the inhaler into contact with the oral mucosa (lips, mouth/pharynx). This is found to be a problem in that the oral mucosa in all people contain a variably large number of different bacteria and other microorganisms, which may be pathogens. Accordingly, the mouthpiece of the inhaler becomes contaminated when used. Patients, and accordingly the users of inhalers, are encouraged to clean the mouthpiece after using the inhaler, but the cleaning operation is carried out with variable consistency depending on the patient's personal approach, his/her age and the severity of his/her illness. Moreover, the inside of the housing of the inhaler also has to be cleaned, in particular in order to remove medicament residues, because such residues can lead to regulatory problems if they become detached at irregular intervals and are discharged with the actual dose.

DE 693 19 100 T2 discloses a disposable inhaler which is to be activated by breathing and which comprises a tubular housing having two parts forming an air duct which is open at both ends, one end forming an air inlet and the other end forming an air outlet. The housing has a compartment for storing a pharmaceutical powder for inhalation and is provided with a narrow portion adjacent to the compartment in order to achieve a turbulent air flow at the narrow portion on inhalation, by which the powder is lifted out of the compartment and mixed with the air stream. The compartment is in the form of an indentation adjacent to the air inlet and communicates with the ambient air by way of a through-hole in its base. The indentation and the through-hole are covered in an air-tight manner with a sealing film, it being possible to remove the film from the outside.

BRIEF SUMMARY OF THE INVENTION

It is an object of the invention to provide an inhaler of the type mentioned at the beginning which is easy for a patient to handle while having a simple and inexpensive construction.

DETAILED DESCRIPTION

According to the invention, the object is achieved in that the inhalation channel of the upper housing part has a unit for dispersing the pulverulent medicament which is connected to the piercing elements, the upper housing part being displaceable relative to the lower housing part in order to open the blister cavity.

The inhaler is advantageous in that it can be produced inexpensively for single use using a small number of individual parts and comprises only components that are absolutely necessary. The unit for dispersion is either produced in one piece with the upper housing part by the injection-moulding process or is connected fixedly and permanently to the inhalation channel by welding, adhesive bonding, pressing or other known joining techniques. The unit for dispersion ensures that the particles of the medicament are distributed finely and in an inhalable manner in the air aspirated by the user. Owing to its design as a single-use inhaler, its handling is simplified because regular cleaning is not necessary and medicament residues, in particular in the inhalation channel and/or in the unit for dispersion, cannot impair the delivery of the medicament. The upper housing part, and accordingly also the mouthpiece, can be in the form of a simple tube without an ergonomic design and, like the lower housing part, can be made of a plastics material. The plastics materials are preferably polymers, thermoplastic polycondensation products, polyadducts, modified natural materials or rubbers or mixtures of these plastics materials. Particular preference is given to polyolefins, vinyl chloride polymers, styrene polymers, polyacetals, polyamides, thermoplastic polyesters and polyaryl ethers or mixtures of these plastics materials. Examples of these plastics materials are polyethylene, polyvinyl chloride, polyoxy-methylene, polyacetal, acrylonitrile/butadiene/styrene (ABS), acrylonitrile/styrene/acrylic ester (ASA), polyamides, polycarbonate, poly(ethylene terephthalate); poly(butylene terephthalate) or poly(phenylene ether). Such plastics materials can be obtained, for example, from Ensinger in Germany, Nufringen.

Inhalers are known under the trade names HandiHaler®, Spinhaler®, Rotahaler®, Aerolizer®, Flowcaps®, Turbospin®, AIR DPI®, Orbital®, Directhaler® and/or are described in DE 33 45 722, EP 0 591 136, DE 43 18 455, WO 91/02558, FR-A-2 146 202, US-A-4 069 819, EP 666085, EP 869079, U.S. Pat. No. 3,991,761, WO 99/45987, WO 20051672, Bell, J. Pharm. Sci. 60, 1559 (1971); Cox, Brit. Med. J. 2, 634 (1969). There are known as powder inhalers single- or multi-dose powder inhalers, in particular Spinhaler®, Rotahaler®, Aerolizer®, Inhalator®, HandiHaler®, Diskhaler®, Diskus®, Accuhaler®, Aerohaler®, Eclipse®, Turbohaler®, Turbuhaler®, Easyhaler®, Novolizer®, Clickhaler®, Pulvinal®, Novolizer®, SkyeHaler®, Xcelovair®, Pulvina®, Taifun®, MAG-haler®, Twisthaler® and Jethaler®.

The compounds mentioned hereinbelow can be used in the device according to the invention on their own or in combination. In the compounds mentioned hereinbelow, W is a pharmacologically active ingredient and is selected (for example) from the group consisting of betamimetics, anticholinergics, corticosteroids, PDE4 inhibitors, LTD4 antagonists, EGFR inhibitors, dopamine agonists, H1-antihistamines, PAF antagonists and PI3 kinase inhibitors. Double or triple combinations of W can further be combined and used in the device according to the invention. Combinations of W mentioned by way of example would be:

W represents a betamimetic combined with an anticholinergic, corticosteroid, PDE4 inhibitor, EGFR inhibitor or LTD4 antagonist, W represents an anticholinergic combined with a betamimetic, corticosteroid, PDE4 inhibitor, EGFR inhibitor or LTD4 antagonist, W represents a corticosteroid combined with a PDE4 inhibitor, EGFR inhibitor or LTD4 antagonist, W represents a PDE4 inhibitor combined with an EGFR inhibitor or LTD4 antagonist, W represents an EGFR inhibitor combined with an LTD4 antagonist.

As betamimetics there are preferably used compounds selected from the group consisting of albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and 3-(4-{6-[2-hydroxy-2-(4-hydroxy-3-hydroxymethyl-phenyl)-ethylamino]-hexyloxy}-butyl)-benzyl-sulfonamide 5-[2-(5,6-diethyl-indan-2-ylamino)-1-hydroxy-ethyl]-8-hydroxy-1H-quinolin-2-one 4-hydroxy-7-[2-{[2-{[3-(2-phenylethoxy)propyl]sulfonyl}-ethyl]-amino}ethyl]-2(3H)-benzothiazolone 1-(2-fluoro-4-hydroxyphenyl)-2-[4-(1-benzimidazolyl)-2-methyl-2-butylamino]ethanol 1-[3-(4-methoxybenzyl-amino)-4-hydroxyphenyl]-2-[4-(1-benzimidazolyl)-2-methyl-2-butylamino]ethanol 1-[2H-5-hydroxy-3-oxo-4H-1,4-benzoxazin-8-yl]-2-[3-(4-N,N-dimethylaminophenyl)-2-methyl-2-propylamino]ethanol 1-[2H-5-hydroxy-3-oxo-4H-1,4-benzoxazin-8-yl]-2-(3-(4-methoxyphenyl)-2-methyl-2-propylamino]ethanol 1-[2H-5-hydroxy-3-oxo-4H-1,4-benzoxazin-8-yl]-2-[3-(4-n-butyloxyphenyl)-2-methyl-2-propylamino]ethanol 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol 5-hydroxy-8-(1-hydroxy-2-isopropylaminobutyl)-2H-1,4-benzoxazin-3-(4H)-one 1-(4-amino-3-chloro-5-trifluoromethylphenyl)-2-tert-butylamino)ethanol 6-hydroxy-8-{1-hydroxy-2-[2-(4-methoxy-phenyl)-1,1-dimethyl-ethylamino]-ethyl}-4H-benzo[1,4]oxazin-3-one 6-hydroxy-8-{1-hydroxy-2-[2-(4-phenoxy-acetic acid ethyl ester) 1,1-dimethylethylamino]-ethyl}-4H-benzo[1,4]-oxazin-3-one 6-hydroxy-8-{1-hydroxy-2-[2-(4-phenoxyacetic acid) 1,1-dimethyl-ethylamino]-ethyl}-4H-benzo[1,4]oxazin-3-one 8-{2-[1,1-dimethyl-2-(2,4,6-trimethylphenyl)-ethylamino]-1-hydroxy-ethyl}-6-hydroxy-4H-benzo[1,4]oxazin-3-one 6-hydroxy-8-{1-hydroxy-2-[2-(4-hydroxy-phenyl)-1,1-dimethyl-ethylamino]-ethyl}-4H-benzo[1,4]oxazin-3-one 6-hydroxy-8-{1-hydroxy-2-[2-(4-isopropyl-phenyl)-1,1-dimethyl-ethylamino]-ethyl}-4H-benzo[1,4]oxazin-3-one 8-{2-[2-(4-ethyl-phenyl)-1,1-dimethyl-ethylamino]-1-hydroxy-ethyl}-6-hydroxy-4H-benzo[1,4]oxazin-3-one 8-{2-[2-(4-ethoxy-phenyl)-1,1-dimethyl-ethylamino]-1-hydroxy-ethyl}-6-hydroxy-4H-benzo[1,4]oxazin-3-one 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid 8-{2-[2-(3,4-difluoro-phenyl)-1,1-dimethyl-ethylamino]-1-hydroxy-ethyl}-6-hydroxy-4H-benzo[1,4]oxazin-3-one 1-(4-ethoxy-carbonylamino-3-cyano-5-fluorophenyl)-2-(tert-butylamino)ethanol 2-hydroxy-5-(1-hydroxy-2-{2-[4-(2-hydroxy-2-phenyl-ethyl-amino)-phenyl]-ethylamino}-ethyl)-benzaldehyde N-[2-hydroxy-5-(1-hydroxy-2-{2-[4-(2-hydroxy-2-phenylethylamino)-phenyl]-ethylamino}-ethyl)-phenyl]-formamide 8-hydroxy-5-(1-hydroxy-2-{2-[4-(6-methoxy-biphenyl-3-yl-amino)-phenyl]-ethylamino}-ethyl)-1H-quinolin-2-one 8-hydroxy-5-[1-hydroxy-2-(6-phenylethylamino-hexylamino)-ethyl]-1H-quinolin-2-one 5-[2-(2-{4-[4-(2-amino-2-methyl-propoxy)-phenylamino]-phenyl}-ethylamino)-1-hydroxy-ethyl]-8-hydroxy-1H-quinolin-2-one

[3-(4-{6-[2-hydroxy-2-(4-hydroxy-3-hydroxymethyl-phenyl)-ethylamino]-hexyloxy}-butyl)-5-methyl-phenyl]-urea 4-(2-{6-[2-(2,6-dichloro-benzyloxy)-ethoxy]-hexylamino}-1-hydroxy-ethyl)-2-hydroxymethyl-phenol 3-(4-{6-[2-hydroxy-2-(4-hydroxy-3-hydroxymethyl-phenyl)-ethylamino]-hexyloxy}-butyl)-benzylsulfonamide 3-(3-{7-[2-hydroxy-2-(4-hydroxy-3-hydroxymethyl-phenyl)-ethylamino]-heptyloxy}-propyl)-benzylsulfonamide 4-(2-{6-[4-(3-cyclopentanesulfonyl-phenyl)-butoxy]-hexylamino}-1-hydroxyethyl)-2-hydroxymethyl-phenol N-adamantan-2-yl-2-(3-{2-[2-hydroxy-2-(4-hydroxy-3-hydroxymethyl-phenyl)-ethylamino]-propyl}-phenyl)-acetamide, optionally in the form of their racemates, enantiomers, diastereoisomers and optionally in the form of their pharmacologically acceptable acid addition salts, solvates or hydrates. Preference is given according to the invention to the acid addition salts of the betamimetics selected from the group consisting of hydrochloride, hydrobromide, hydroiodide, hydrosulfate, hydrophosphate, hydromethane-sulfonate, hydronitrate, hydromaleate, hydroacetate, hydro-citrate, hydrofumarate, hydrotartrate, hydrooxalate, hydro-succinate, hydrobenzoate and hydro-p-toluenesulfonate.

As anticholinergics there are preferably used compounds selected from the group consisting of tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts, the cations represent the pharmacologically active constituent. The above-mentioned salts can preferably contain as anions chloride, bromide, iodide, sulfate, phosphate, methanesulfonate, nitrate, maleate, acetate, citrate, fumarate, tartrate, oxalate, succinate, benzoate or p-toluenesulfonate, with chloride, bromide, iodide, sulfate, methanesulfonate or p-toluene-sulfonate being preferred as counter-ions. Of all the salts, the chlorides, bromides, iodides and methane-sulfonates are particularly preferred.

Anticholinergics that are likewise preferred are selected from the salts of formula AC-1

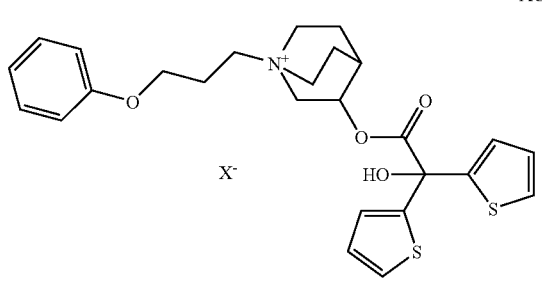

AC-1 wherein X⁻ represents a negatively charged anion, preferably an anion selected from the group consisting of fluoride, chloride, bromide, iodide, sulfate, phosphate, methane-sulfonate, nitrate, maleate, acetate, citrate, fumarate, tartrate, oxalate, succinate, benzoate and p-toluene-sulfonate, preferably a singly negatively charged anion, particularly preferably an anion selected from the group consisting of fluoride, chloride, bromide, methanesulfonate and p-toluenesulfonate, especially preferably bromide, optionally in the form of their racemates, enantiomers or hydrates. Medicament combinations that contain the enantiomers of formula AC-1-en

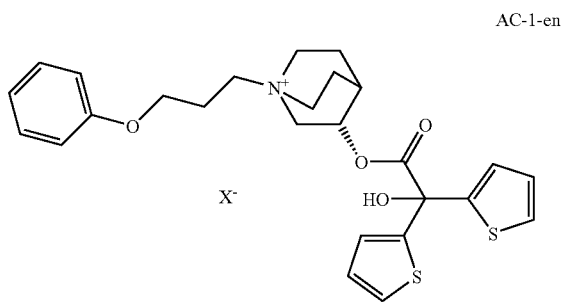

AC-1-en wherein X⁻ can have the meanings mentioned above, are of particular importance. Further preferred anticholinergics are selected from the salts of formula AC-2

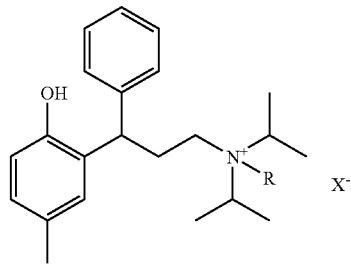

AC-2 wherein R can represent either methyl or ethyl and wherein X⁻ can have the meanings mentioned above. In an alternative embodiment, the compound of formula AC-2 can also be in the form of the free base AC-2-base

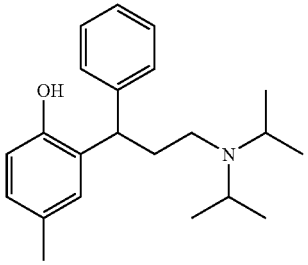

AC-2-base

Further mentioned compounds are:
2,2-diphenylpropionic acid tropenol ester methobromide
2,2-diphenylpropionic acid scopine ester methobromide
2-fluoro-2,2-diphenylacetic acid scopine ester methobromide
2-fluoro-2,2-diphenylacetic acid tropenol ester methobromide
3,3',4,4'-tetrafluorobenzilic acid tropenol ester methobromide
3,3',4,4'-tetrafluorobenzilic acid scopine ester methobromide
4,4'-difluorobenzilic acid tropenol ester methobromide
4,4'-difluorobenzilic acid scopine ester methobromide
3,3'-difluorobenzilic acid tropenol ester methobromide
3,3'-difluorobenzilic acid scopine ester methobromide
9-hydroxy-fluorene-9-carboxylic acid tropenol ester methobromide
9-fluoro-fluorene-9-carboxylic acid tropenol ester methobromide
9-hydroxy-fluorene-9-carboxylic acid scopine ester methobromide
9-fluoro-fluorene-9-carboxylic acid scopine ester methobromide
9-methyl-fluorene-9-carboxylic acid tropenol ester methobromide
9-methyl-fluorene-9-carboxylic acid scopine ester methobromide
benzilic acid cyclopropyltropine ester methobromide
2,2-diphenylpropionic acid cyclopropyltropine ester methobromide
9-hydroxy-xanthene-9-carboxylic acid cyclopropyltropine ester methobromide
9-methyl-fluorene-9-carboxylic acid cyclopropyltropine ester methobromide
9-methyl-xanthene-9-carboxylic acid cyclopropyltropine ester methobromide
9-hydroxy-fluorene-9-carboxylic acid cyclopropyltropine ester methobromide
4,4'-difluorobenzilic acid methyl ester cyclopropyltropine ester methobromide
9-hydroxy-xanthene-9-carboxylic acid tropenol ester methobromide
9-hydroxy-xanthene-9-carboxylic acid scopine ester methobromide
9-methyl-xanthene-9-carboxylic acid tropenol ester methobromide
9-methyl-xanthene-9-carboxylic acid scopine ester methobromide
9-ethyl-xanthene-9-carboxylic acid tropenol ester methobromide
9-difluoromethyl-xanthene-9-carboxylic acid tropenol ester methobromide
9-hydroxymethyl-xanthene-9-carboxylic acid scopine ester methobromide.

The above-mentioned compounds can also be used within the scope of the present invention in the form of salts in which the salts metho-X are used instead of methobromide, wherein X can have the meanings mentioned above for X⁻.

As corticosteroids there are preferably used compounds selected from the group consisting of beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, RPR-106541, NS-126, ST-26 and 6,9-difluoro-17-[(2-furanylcarbonyl)oxy]-11-hydroxy-16-methyl-3-oxo-androsta-1,4-diene-17-carbothionic acid (S)-fluoromethyl ester 6,9-difluoro-1'-hydroxy-16-methyl-3-oxo-17-propionyloxy-androsta-1,4-diene-17-carbothionic acid (S)-(2-oxo-tetrahydro-furan-3S-yl) ester, 6α,9α-difluoro-11β-hydroxy-16α-methyl-3-oxo-17α-(2,2,3,3-tetramethylcyclopropylcarbonyl)oxy-androsta-1,4-diene-17β-carboxylic acid cyanomethyl ester, optionally in the form of their racemates, enantiomers or diastereoisomers and optionally in the form of their salts and derivatives, their solvates and/or hydrates. Any reference to steroids includes a reference to any salts or derivatives, hydrates or solvates thereof that may exist. Examples of possible salts and derivatives of the steroids can be: alkali salts, such as, for example, sodium or potassium salts, sulfobenzoates, phosphates, isonicotinates, acetates, dichloroacetates, propionates, dihydrogen phosphates, palmitates, pivalates or furoates.

As PDE4 inhibitors there are preferably used compounds selected from the group consisting of enprofyllin, theophyllin, roflumilast, ariflo (cilomilast), tofimilast, pumafentrin, lirimilast, arofyllin, atizoram, D-4418, Bay-198004, BY343, CP-325,366, D-4396 (Sch-351591), AWD-12-281 (GW-842470), NCS-613, CDP-840, D-4418, PD-168787, T-440, T-2585, V-11294A, CI-1018, CDC-801, CDC-3052, D-22888, YM-58997, Z-15370 and N-(3,5-dichloro-1-oxo-pyridin-4-yl)-4-difluoromethoxy-3-cyclopropylmethoxybenzamide (−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide (R)-(+)-1-(4-bromobenzyl)-4-[(3-cyclopentyloxy)-4-methoxyphenyl]-2-pyrrolidone 3-(cyclopentyloxy-4-methoxyphenyl)-1-(4-N'-[N-2-cyano-S-methyl-isothioureido]benzyl)-2-pyrrolidone cis[4-cyano-4-(3-cyclopentyloxy-4-methoxyphenyl)cyclohexane-1-carboxylic acid]

2-carbomethoxy-4-cyano-4-(3-cyclopropylmethoxy-4-difluoromethoxyphenyl)cyclohexan-1-one cis[4-cyano-4-(3-cyclopropylmethoxy-difluoromethoxyphenyl)cyclohexan-1-ol]

(R)-(+)-ethyl[4-(3-cyclopentyloxy-4-methoxyphenyl)-pyrrolidin-2-ylidene]acetate (S)-(−)-ethyl[4-(3-cyclopentyloxy-4-methoxyphenyl)-pyrrolidin-2-ylidene]acetate 9-cyclopentyl-5,6-dihydro-7-ethyl-3-(2-thienyl)-9H-pyrazolo[3,4-c]-1,2,4-triazolo[4,3-a]pyridine 9-cyclopentyl-5,6-dihydro-7-ethyl-3-(tert-butyl)-9H-pyrazolo[3,4-c]-1,2,4-triazolo[4,3-a]pyridine, optionally in the form of their racemates, enantiomers, diastereoisomers and optionally in the form of their pharmacologically acceptable acid addition salts, solvates or hydrates. Preference is given according to the invention to the acid addition salts of the PDE4 inhibitors selected from the group consisting of hydrochloride, hydrobromide, hydroiodide, hydrosulfate, hydrophosphate, hydromethane-sulfonate, hydronitrate, hydromaleate, hydroacetate, hydro-citrate, hydrofumarate, hydrotartrate, hydrooxalate, hydro-succinate, hydrobenzoate and hydro-p-toluenesulfonate.

As LTD4 antagonists there are preferably used compounds selected from the group consisting of montelukast, pranlukast, zafirlukast, MCC-847 (ZD-3523), MN-001, MEN-91507 (LM-1507), WF-5078, VUF-K-8707, L-733321 and 1-(((R)-3-(2-(6,7-difluoro-2-quinolinyl)ethenyl)phenyl)-3-(2-(2-hydroxy-2-propyl)phenyl)thio)methylcyclopropane-acetic acid 1-(((1(R)-3-(2-(2,3-dichlorothieno[3,2-b]pyridin-5-yl)-(E)-ethenyl)phenyl)-3-(2-(1-hydroxy-1-methylethyl)-phenyl)propyl)thio)methyl)cyclopropaneacetic acid

[2-[[2-(4-tert-butyl-2-thiazolyl)-5-benzofuranyl]oxy-methyl]phenyl]acetic acid, optionally in the form of their racemates, enantiomers, diastereoisomers and optionally in the form of their pharmacologically acceptable acid addition salts, solvates or hydrates. According to the invention, these acid addition salts are preferably selected from the group consisting of hydrochloride, hydrobromide, hydroiodide, hydrosulfate, hydrophosphate, hydromethanesulfonate, hydro-nitrate, hydromaleate, hydroacetate, hydrocitrate, hydro-fumarate, hydrotartrate, hydrooxalate, hydrosuccinate, hydrobenzoate and hydro-p-toluenesulfonate. Salts or derivatives for the formation of which the LTD4 antagonists are optionally capable are understood as being, for example: alkali salts, such as, for example, sodium or potassium salts, alkaline earth salts, sulfobenzoates, phosphates, isonicotinates, acetates, propionates, dihydrogen phosphates, palmitates, pivalates or furoates.

As EGFR inhibitors there are preferably used compounds selected from the group consisting of cetuximab, trastuzumab, ABX-EGF, Mab ICR-62 and 4-[(3-chloro-4-fluorophenyl)amino]-6-{[4-(morpholin-4-yl)-1-oxo-2-buten-1-yl]-amino}-7-cyclopropylmethoxy-quinazoline 4-[(3-chloro-4-fluorophenyl)amino]-6-{[4-(N,N-dimethyl-amino)-1-oxo-2-buten-1-yl]-amino}-7-cyclopropyl-methoxy-quinazoline 4-[(3-chloro-4-fluorophenyl)amino]-6-{[4-(N,N-dimethyl-amino)-1-oxo-2-buten-1-yl]-amino}-7-cyclopropyl-methoxy-quinazoline 4-[(R)-(1-phenyl-ethyl)amino]-6-{[4-(morpholin-4-yl)-1-oxo-2-buten-1-yl]-amino}-7-cyclopentyloxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline 4-[(3-chloro-4-fluoro-phenyl)amino]-6-{[4-((R)-2-meth-oxy-methyl-6-oxo-morpholin-4-yl)-1-oxo-2-buten-1-yl]amino}-7-cyclopropylmethoxy-quinazoline 4-[(3-chloro-4-fluoro-phenyl)amino]-6-[2-((S)-6-methyl-2-oxo-morpholin-4-yl)-ethoxy]-7-methoxy-quinazoline 4-[(3-chloro-4-fluorophenyl)amino]-6-{[4-[N-(2-methoxy-ethyl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethyl-amino)-1-oxo-2-buten-1-yl]amino}-7-cyclopentyloxy-quinazoline 4-[(R)-(1-phenyl-ethyl)amino]-6-{[4-(N,N-bis-(2-methoxy-ethyl)-amino)-1-oxo-2-buten-1-yl]amino}-7-cyclopro-pyl-methoxy-quinazoline 4-[(R)-(1-phenyl-ethyl)amino]-6-({4-[N-(2-methoxy-ethyl)-N-ethyl-amino]-1-oxo-2-buten-1-yl}amino)-7-cyclopropyl-methoxy-quinazoline 4-[(R)-(1-phenyl-ethyl)amino]-6-({4-[N-(2-methoxy-ethyl)-N-methyl-amino]-1-oxo-2-buten-1-yl}amino)-7-cyclopropyl-methoxy-quinazoline
4-[(R)-(1-phenyl-ethyl)amino]-6-({4-[N-(tetrahydropyran-4-yl)-N-methyl-amino]-1-oxo-2-buten-1-yl}amino)-7-cyclo-propylmethoxy-quinazoline
4-[(3-chloro-4-fluorophenyl)amino]-6-{[4-(N,N-dimethyl-amino)-1-oxo-2-buten-1-yl]amino}-7-((R)-tetrahydrofuran-3-yloxy)-quinazoline
4-[(3-chloro-4-fluorophenyl)amino]-6-{[4-(N,N-dimethyl-amino)-1-oxo-2-buten-1-yl]amino}-7-((S)-tetrahydrofuran-3-yloxy)-quinazoline
4-[(3-chloro-4-fluorophenyl)amino]-6-({4-[N-(2-methoxy-ethyl)-N-methylamino]-1-oxo-2-buten-1-yl}amino)-7-cyclopentyloxy-quinazoline
4-[(3-chloro-4-fluorophenyl)amino]-6-{[4-(N-cyclopropyl-N-methyl-amino)-1-oxo-2-buten-1-yl]amino}-7-cyclopentyl-oxy-quinazoline
4-[(3-chloro-4-fluorophenyl)amino]-6-{[4-(N,N-dimethyl-amino)-1-oxo-2-buten-1-yl]amino}-7-[(R)-(tetrahydrofuran-2-yl)methoxy]-quinazoline
4-[(3-chloro-4-fluorophenyl)amino]-6-{[4-(N,N-dimethyl-amino)-1-oxo-2-buten-1-yl]amino}-7-[(S)-(tetrahydrofuran-2-yl)methoxy]-quinazoline
4-[(3-ethynyl-phenyl)amino]-6,7-bis-(2-methoxy-ethoxy)-quinazoline
4-[(3-chloro-4-fluorophenyl)amino]-7-[3-(morpholin-4-yl)-propyloxy]-6-[(vinylcarbonyl)amino]-quinazoline
4-[(R)-(1-phenyl-ethyl)amino]-6-(4-hydroxy-phenyl)-7H-pyrrolo[2,3-d]pyrimidine
3-cyano-4-[(3-chloro-4-fluorophenyl)amino]-6-{[4-(N,N-dimethylamino)-1-oxo-2-buten-1-yl]amino}-7-ethoxy-quinoline
4-{[3-chloro-4-(3-fluoro-benzyloxy)-phenyl]amino}-6-(5-{[(2-methanesulfonylethyl)amino]methyl}-furan-2-yl)-quinazoline
4-[(R)-(1-phenyl-ethyl)amino]-6-{[4-((R)-6-methyl-2-oxo-morpholin-4-yl)-1-oxo-2-buten-1-yl]amino}-7-methoxy-quinazoline
4-[(3-chloro-4-fluorophenyl)amino]-6-{[4-(morpholin-4-yl)-1-oxo-2-buten-1-yl]amino}-7-[(tetrahydrofuran-2-yl)-methoxy]-quinazoline
4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline
4-[(3-ethynyl-phenyl)amino]-6-{[4-(5,5-dimethyl-2-oxo-morpholin-4-yl)-1-oxo-2-buten-1-yl]amino}-quinazoline
4-[(3-chloro-4-fluoro-phenyl)amino]-6-[2-(2,2-dimethyl-6-oxo-morpholin-4-yl)ethoxy]-7-methoxy-quinazoline
4-[(3-chloro-4-fluoro-phenyl)amino]-6-[2-(2,2-dimethyl-6-oxo-morpholin-4-yl)ethoxy]-7-[(R)-(tetrahydrofuran-2-yl)methoxy]-quinazoline
4-[(3-chloro-4-fluoro-phenyl)amino]-7-[2-(2,2-dimethyl-6-oxo-morpholin-4-yl)ethoxy]-6-[(S)-(tetrahydrofuran-2-yl)-methoxy]-quinazoline
4-[(3-chloro-4-fluoro-phenyl)amino]-6-{2-[4-(2-oxo-morpholin-4-yl)-piperidin-1-yl]ethoxy}-7-methoxy-quinazoline
4-[(3-chloro-4-fluoro-phenyl)amino]-6-[1-(tert-butyloxy-carbonyl)-piperidin-4-yloxy]-7-methoxy-quinazoline
4-[(3-chloro-4-fluoro-phenyl)amino]-6-(trans-4-amino-cyclohexan-1-yloxy)-7-methoxy-quinazoline
4-[(3-chloro-4-fluoro-phenyl)amino]-6-(trans-4-methanesulfonylamino-cyclohexan-1-yloxy)-7-methoxy-quinazoline
4-[(3-chloro-4-fluoro-phenyl)amino]-6-(tetrahydropyran-3-yloxy)-7-methoxy-quinazoline
4-[(3-chloro-4-fluoro-phenyl)amino]-6-(1-methyl-piperidin-4-yloxy)-7-methoxy-quinazoline
4-[(3-chloro-4-fluoro-phenyl)amino]-6-{1-[(morpholin-4-yl)carbonyl]-piperidin-4-yl-oxy}-7-methoxy-quinazoline
4-[(3-chloro-4-fluoro-phenyl)amino]-6-{1-[(methoxy-methyl)carbonyl]-piperidin-4-yloxy}-7-methoxy-quinazoline
4-[(3-chloro-4-fluoro-phenyl)amino]-6-(piperidin-3-yloxy)-7-methoxy-quinazoline
4-[(3-chloro-4-fluoro-phenyl)amino]-6-[1-(2-acetylamino-ethyl)-piperidin-4-yloxy]-7-methoxy-quinazoline
4-[(3-chloro-4-fluoro-phenyl)amino]-6-(tetrahydropyran-4-yloxy)-7-ethoxy-quinazoline
4-[(3-chloro-4-fluoro-phenyl)amino]-6-((S)-tetrahydro-furan-3-yloxy)-7-hydroxy-quinazoline
4-[(3-chloro-4-fluoro-phenyl)amino]-6-(tetrahydropyran-4-yloxy)-7-(2-methoxyethoxy)-quinazoline
4-[(3-chloro-4-fluoro-phenyl)amino]-6-{trans-4-[(dimethylamino)sulfonylamino]-cyclohexan-1-yloxy}-7-methoxy-quinazoline
4-[(3-chloro-4-fluoro-phenyl)amino]-6-{trans-4-[(morpholin-4-yl)carbonylamino]-cyclohexan-1-yloxy}-7-methoxy-quinazoline
4-[(3-chloro-4-fluoro-phenyl)amino]-6-{trans-4-[(morpholin-4-yl)sulfonylamino]-cyclohexan-1-yloxy}-7-methoxy-quinazoline
4-[(3-chloro-4-fluoro-phenyl)amino]-6-(tetrahydropyran-4-yloxy)-7-(2-acetylaminoethoxy)-quinazoline
4-[(3-chloro-4-fluoro-phenyl)amino]-6-(tetrahydropyran-4-yloxy)-7-(2-methanesulfonylamino-ethoxy)-quinazoline
4-[(3-chloro-4-fluoro-phenyl)amino]-6-{1-[(piperidin-1-yl)carbonyl]-piperidin-4-yloxy}-7-methoxy-quinazoline
4-[(3-chloro-4-fluoro-phenyl)amino]-6-(1-aminocarbonyl-methyl-piperidin-4-yloxy)-7-methoxy-quinazoline
4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline
4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline
4-[(3-chloro-4-fluoro-phenyl)amino]-6-(cis-4-{N-[(morpholin-4-yl)sulfonyl]-N-methyl-amino}-cyclohexan-1-yloxy)-7-methoxy-quinazoline
4-[(3-chloro-4-fluoro-phenyl)amino]-6-(trans-4-ethane-sulfonylamino-cyclohexan-1-yloxy)-7-methoxy-quinazoline
4-[(3-chloro-4-fluoro-phenyl)amino]-6-(1-methanesulfonyl-piperidin-4-yloxy)-7-ethoxy-quinazoline
4-[(3-chloro-4-fluoro-phenyl)amino]-6-(1-methanesulfonyl-piperidin-4-yloxy)-7-(2-methoxy-ethoxy)-quinazoline
4-[(3-chloro-4-fluoro-phenyl)amino]-6-[1-(2-methoxy-acetyl)-piperidin-4-yloxy]-7-(2-methoxy-ethoxy)-quinazoline
4-[(3-chloro-4-fluoro-phenyl)amino]-6-(cis-4-acetylamino-cyclohexan-1-yloxy)-7-methoxy-quinazoline
4-[(3-ethynyl-phenyl)amino]-6-[1-(tert-butyloxycarbonyl)-piperidin-4-yloxy]-7-methoxy-quinazoline
4-[(3-ethynyl-phenyl)amino]-6-(tetrahydropyran-4-yloxy]-7-methoxy-quinazoline
4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline
4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline 4-[(3-chloro-4-fluoro-phenyl)amino]-6-{cis-4-[(morpholin-4-yl)carbonylamino]-cyclohexan-1-yloxy}-7-methoxy-quinazoline 4-[(3-chloro-4-fluoro-phenyl)amino]-6-{1-[2-(2-oxo-pyrrolidin-1-yl)ethyl]-piperidin-4-yloxy}-7-methoxy-quinazoline 4-[(3-chloro-4-fluoro-phenyl)amino]-6-{1-[(morpholin-4-yl)carbonyl]-piperidin-4-yloxy}-7-(2-methoxy-ethoxy)-quinazoline 4-[(3-ethynyl-phenyl)amino]-6-(1-acetyl-piperidin-4-yloxy)-7-methoxy-quinazoline 4-[(3-ethynyl-phenyl)amino]-6-(1-methyl-piperidin-4-yloxy)-7-methoxy-quinazoline 4-[(3-ethynyl-phenyl)amino]-6-(1-methanesulfonyl-piperidin-4-yloxy)-7-methoxy-quinazoline 4-[(3-chloro-4-fluoro-phenyl)amino]-6-(1-methyl-piperidin-4-yloxy)-7-(2-methoxy-ethoxy)-quinazoline 4-[(3-chloro-4-fluoro-phenyl)amino]-6-(1-isopropyloxycarbonyl-piperidin-4-yloxy)-7-methoxy-quinazoline 4-[(3-chloro-4-fluoro-phenyl)amino]-6-(cis-4-methylamino-cyclohexan-1-yloxy)-7-methoxy-quinazoline 4-[(3-chloro-4-fluoro-phenyl)amino]-6-{cis-4-[N-(2-methoxy-acetyl)-N-methylamino]-cyclohexan-1-yloxy}-7-methoxy-quinazoline 4-[(3-ethynyl-phenyl)amino]-6-(piperidin-4-yloxy)-7-methoxy-quinazoline 4-[(3-ethynyl-phenyl)amino]-6-[1-(2-methoxy-acetyl)-piperidin-4-yloxy]-7-methoxy-quinazoline 4-[(3-ethynyl-phenyl)amino]-6-{1-[(morpholin-4-yl)-carbonyl]-piperidin-4-yloxy}-7-methoxy-quinazoline 4-[(3-chloro-4-fluoro-phenyl)amino]-6-{1-[(cis-2,6-dimethyl-morpholin-4-yl)carbonyl]-piperidin-4-yloxy}-7-methoxy-quinazoline 4-[(3-chloro-4-fluoro-phenyl)amino]-6-{1-[(2-methyl-morpholin-4-yl)carbonyl]-piperidin-4-yloxy}-7-methoxy-quinazoline 4-[(3-chloro-4-fluoro-phenyl)amino]-6-{1-[(S,S)-(2-oxa-5-aza-bicyclo[2.2.1]hept-5-yl)carbonyl]-piperidin-4-yloxy}-7-methoxy-quinazoline 4-[(3-chloro-4-fluoro-phenyl)amino]-6-{1-[(N-methyl-N-2-methoxyethylamino)carbonyl]-piperidin-4-yloxy}-7-methoxy-quinazoline 4-[(3-chloro-4-fluoro-phenyl)amino]-6-(1-ethyl-piperidin-4-yloxy)-7-methoxy-quinazoline 4-[(3-chloro-4-fluoro-phenyl)amino]-6-{1-[(2-methoxyethyl)carbonyl]-piperidin-4-yloxy}-7-methoxy-quinazoline 4-[(3-chloro-4-fluoro-phenyl)amino]-6-{1-[(3-methoxypropyl-amino)-carbonyl]-piperidin-4-yloxy}-7-methoxy-quinazoline 4-[(3-chloro-4-fluoro-phenyl)amino]-6-[cis-4-(N-methanesulfonyl-N-methyl-amino)-cyclohexan-1-yloxy]-7-methoxy-quinazoline 4-[(3-chloro-4-fluoro-phenyl)amino]-6-[cis-4-(N-acetyl-N-methyl-amino)-cyclohexan-1-yloxy]-7-methoxy-quinazoline 4-[(3-chloro-4-fluoro-phenyl)amino]-6-(trans-4-methylamino-cyclohexan-1-yloxy)-7-methoxy-quinazoline 4-[(3-chloro-4-fluoro-phenyl)amino]-6-[trans-4-(N-methanesulfonyl-N-methyl-amino)-cyclohexan-1-yloxy]-7-methoxy-quinazoline 4-[(3-chloro-4-fluoro-phenyl)amino]-6-(trans-4-dimethylamino-cyclohexan-1-yloxy)-7-methoxy-quinazoline 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline 4-[(3-chloro-4-fluoro-phenyl)amino]-6-(1-methanesulfonyl-piperidin-4-yloxy)-7-methoxy-quinazoline 4-[(3-chloro-4-fluoro-phenyl)amino]-6-(1-cyano-piperidin-4-yloxy)-7-methoxy-quinazoline, optionally in the form of their racemates, enantiomers, diastereoisomers and optionally in the form of their pharmacologically acceptable acid addition salts, solvates or hydrates. According to the invention, these acid addition salts are preferably selected from the group consisting of hydrochloride, hydrobromide, hydroiodide, hydrosulfate, hydrophosphate, hydromethanesulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

As dopamine agonists there are preferably used compounds selected from the group consisting of bromocriptin, cabergoline, alpha-dihydroergocryptin, lisuride, pergolide, pramipexol, roxindol, ropinirol, talipexol, terguride and viozan, optionally in the form of their racemates, enantiomers, diastereoisomers and optionally in the form of their pharmacologically acceptable acid addition salts, solvates or hydrates. According to the invention, these acid addition salts are preferably selected from the group consisting of hydrochloride, hydrobromide, hydroiodide, hydrosulfate, hydrophosphate, hydromethanesulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

As H1-antihistamines there are preferably used compounds selected from the group consisting of epinastine, cetirizine, azelastine, fexofenadine, levocabastine, loratidine, mizolastine, ketotifen, emedastine, dimetindene, clemastine, bamipine, cexchlorpheniramine, pheniramine, doxylamine, chlorphenoxamine, dimenhydrinate, diphenhydramine, promethazine, ebastine, desloratidine and meclozine, optionally in the form of their racemates, enantiomers, diastereoisomers and optionally in the form of their pharmacologically acceptable acid addition salts, solvates or hydrates. According to the invention, these acid addition salts are preferably selected from the group consisting of hydrochloride, hydrobromide, hydroiodide, hydrosulfate, hydrophosphate, hydromethanesulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Any inhalable compounds, such as, for example, also inhalable macromolecules, as disclosed in EP 1 003 478, are used as pharmaceutically active substances, substance formulations or substance mixtures. Preference is given to the use of substances, substance formulations or substance mixtures for the treatment of respiratory diseases that are used in the inhalatory field.

The compound can further originate from the group of the ergot alkaloid derivatives, triptans, CGRP inhibitors, phosphodiesterase V inhibitors, optionally in the form of their racemates, enantiomers or diastereoisomers, optionally in the form of their pharmacologically acceptable acid addition salts, solvates and/or hydrates.

As ergot alkaloid derivatives: dihydroergotamine, ergotamine.

The piercing elements are preferably disposed at a distance from the blister cavity in a position locked by at least one first clip connection between the upper housing part and the lower housing part and, in a position defined by at least one second clip connection, they project into the opened blister cavity. Owing to the first clip connection, the upper housing part is held securely in such a position relative to the lower housing part that unintentional opening of the blister cavity is prevented and, owing to the second clip connection, simple handling of the inhaler on inhalation is ensured because the upper housing part, in the position in which the blister cavity is opened and the inhaler is used as specified for inhaling the medicament, is fixedly held on the lower housing part.

In an embodiment, each piercing element has a triangular tip, one piercing element being arranged in the region of the inhalation channel and one piercing element being arranged offset laterally thereto. The piercing elements, which are substantially in the form of knife points, open the blister cavity in such a manner that, on inhalation, an air stream enters the cavity through one opening and carries the pulverulent medicament through the other opening into the inhalation channel and, from there, to the patient. Because of the shape of the piercing elements, the force to be applied by the user of the inhaler in order to pierce the cover film of the cavity of the blister is comparatively small and the discharge rate of the medicament to be inhaled is ensured.

When the inhaler is to be used only once, it is not absolutely necessary for the piercing elements to have a long working life, that is to say to be suitable for opening a large number of blister cavities. The piercing elements are therefore advantageously made of a plastics material. The piercing elements can, for example, be produced from a semi-finished product or, preferably, they can be manufactured in one piece with the unit for dispersion, for example by the injection-moulding process.

In an alternative embodiment, the piercing elements are made of metal. The metal can be a so-called stainless steel, which is used in the medical field and allows the piercing elements to be made thinner and sharper as compared with a plastics material, as a result of which even a relatively stable cover film covering the cavity of the blister can be pierced.

The piercing elements are preferably punched out of a plate made of metal and are bent at an acute angle to the plate so that they point in the direction towards the blister cavity. The plate with the two piercing elements is easy to handle and fit. Furthermore, the geometry of the piercing elements, in conjunction with their position relative to the cover film of the blister cavity, ensures relatively large flow openings through which almost all of the medicament is discharged from the cavity. The plate is advantageously connected in a positive-locking and/or friction-locked manner to the unit for dispersion. The plate can be, for example, in the form of an insert and can be connected to the unit in an injection-moulding operation. However, it is also possible to provide the plate with two bores which are at a distance from one another and through which there pass plastics pins of the unit for welding. Of course, it is also possible for the plate to be clipped or adhesively bonded to the unit.

The lower housing part advantageously has two opposing clip projections, and corresponding clip openings are let into the upper housing part in different planes. By cooperating with the clip projections, the clip openings determine the position of the lower housing part relative to the upper housing part both in the delivery state of the inhaler, in which the blister cavity is unopened, and in the use state, in which the blister cavity is opened wide by the piercing elements. The clip openings and clip projections are simple to produce without an additional cost outlay and the user has a tactile and visually detectable reminder of the position of the upper housing part relative to the lower housing part, and accordingly of the condition of the inhaler. Furthermore, the clip connections can be of such a size that, on the one hand, unintentional displacement of the upper housing part relative to the lower housing part, and the associated opening of the blister cavity, is prevented and, on the other hand, the blister cavity can be opened with the application of an acceptable force. In order to reduce the force required to displace the upper housing part relative to the lower housing part, the clip projections are arranged at the free ends of opposing locking arms. In order to facilitate opening of the blister cavity, the clip openings are in the form of slots in the plane in which the blister cavity is opened. In the position in which the clip projections reach the slot-like clip openings, the tips of the piercing elements penetrate the cover film of the blister cavity. As the upper housing part and the lower housing part are pressed together within the range determined by the slots, further piercing accompanied by opening of the blister cavity takes place with the application of a relatively small force.

The upper housing part is preferably mounted to be displaceable relative to the lower housing part. The displaceable mounting is simple to produce and is not susceptible to malfunction. An anti-twist means can optionally be provided, which facilitates fitting and handling.

According to a further development, the upper housing part has a cylindrical or elliptical cross-section in which the lower housing part, which is cylindrical or elliptical in cross-section, is mounted and extends conically in the direction towards an air outlet opening, the air inlet opening being formed on the free end face of the lower housing part. The conical form of the cylindrical or elliptical upper housing part ensures that the lips of the user of the inhaler rest tightly on the upper housing part serving as the mouthpiece, whereby a main air stream is aspirated through the inhaler on inhalation. The air outlet opening on the free end face of the lower housing part does not interfere with handling of the inhaler on inhalation because the housing can be gripped at the periphery. In addition, the comparatively simple geometries of the upper housing part and of the lower housing part can be produced with a low outlay.

According to an alternative further development, the upper housing part and the lower housing part are each dish-shaped in cross-section, the lower housing part being mounted in the upper housing part. Accordingly, the housing composed of the upper housing part and the lower housing part is substantially cylindrical. The dish shape, which is simple to produce, also ensures that the lips rest comparatively tightly on the lower housing part.

In order to dispense with additional packaging for the medicament, the blister cavity containing the pulverulent medicament is preferably arranged in the bearing of the housing by the manufacturer. The blister cavity for receiving the medicament has proved to be of value insofar as it provides effective protection from environmental influences.

In order to protect the medicament to be inhaled and the inhaler from environmental influences, the inhaler is provided with an air-tight outer packaging, in particular a film container. Such an outer packaging is commercially available. Alternatively or in addition, the mouthpiece and/or the air inlet opening are closed tightly by a removable cap. As a result of these measures, the inside of the inhaler with the medicament is protected in particular from influences that damage the medicament, such as, for example, moisture, with a minimal outlay in terms of packaging.

In a further embodiment of the invention, the medicament is stored in the blister cavity, viewed in the direction of flow, upstream of the unit for dispersing the pulverulent medicament and passes through a central bore of the unit into the inhalation channel of the mouthpiece, the unit having at least one radial inflow opening which communicates with a flow bore that leads into the inhalation channel. On inhalation, air flows through one opening in the blister cavity and carries the medicament through the other opening in the blister cavity into the central bore of the unit for dispersing the medicament. The air flowing into the unit through the radial inflow opening serves to swirl the medicament, accompanied by fine distribution of the powder particles of the medicament in the flow bore. In the further flow path, the powder particles pass into the inhalation channel, which is formed in the upper housing part of the inhaler, and from there into the lungs of the user of the inhaler. In order to ensure a high delivery rate of the medicament, the central bore of the unit is disposed in alignment with one of the piercing elements.

In order to produce a high flow speed, the central bore is surrounded by an annular space through which air flows and into which the inflow opening leads, the outer wall of the flow bore overlapping an inner wall of the annular space.

In order to produce a directional flow on inhalation, which produces as high a number of small powder particles as possible, two diametrally opposite inflow openings are provided, the width of which is slightly greater than the diameter of the inner wall. In an alternative embodiment, there are provided at least two mutually offset inflow openings which lead into flow channels on opposite sides of the unit which communicate with one another. Mutually opposite cyclonic flows are thus achieved. The inner wall preferably has axial apertures for the flow connection of the bore with the flow bore. It is also possible for the unit to have in its flow bore a deflector plate for the medicament. Alternatively, the deflector plate is fastened to a centering ring inserted into the unit. All the measures for guiding the air flow on inhalation serve to produce as fine a powder as possible by breaking up larger medicament particles.

It will be understood that the features which have been mentioned above and are still to be explained hereinbelow can be used not only in the combination indicated in each case but also in different combinations. The scope of the invention is defined only by the claims.

BRIEF DESCRIPTION OF THE DRAWINGS

The invention is explained in detail hereinbelow by means of some exemplary embodiments with reference to the accompanying drawings, in which:

FIG. 1 shows a front view of an inhaler according to the invention,

FIG. 2 shows a sectional view of the inhaler according to FIG. 1 according to line II-II, FIG. 3 shows a sectional view of the inhaler according to FIG. 1 according to line III-III, FIG. 4 shows a sectional view of the inhaler according to FIG. 1 according to line IV-IV, FIG. 5 shows a side view of the inhaler according to FIG. 1, FIG. 6 shows a sectional view of the inhaler according to FIG. 5 according to line VI-VI, FIG. 7 shows an enlarged side view of the representation of detail VII according to FIG. 6, FIG. 8 shows a sectional view of the detail according to FIG. 7 according to line VIII-VIII, FIG. 9 shows a sectional view of the detail according to FIG. 7 according to line IX-IX, FIG. 10 shows a sectional view of the detail according to FIG. 7 according to line X-X, FIG. 11 shows an enlarged side view of the representation of detail VII according to FIG. 6 in an alternative embodiment, FIG. 12 shows a sectional view of the detail according to FIG. 11 according to line XII-XII, FIG. 13 shows a sectional view of the detail according to FIG. 11 according to line XIIII-XIIII, FIG. 14 shows a sectional view of the detail according to FIG. 11 according to line XIV-XIV, FIG. 15 shows an enlarged side view of the representation of detail VII according to FIG. 6 in a second alternative embodiment, FIG. 16 shows a sectional view of the detail according to FIG. 15 according to line XVI-XVI, FIG. 17 shows a sectional view of the detail according to FIG. 15 according to line XVII-XVII, FIG. 18 shows a sectional view of the detail according to FIG. 15 according to line XVIII-XVIII, FIG. 19 shows an enlarged side view of the representation of detail VII according to FIG. 6 in a third alternative form, FIG. 20 shows a sectional view of the detail according to FIG. 19 according to line XX-XX, FIG. 21 shows a sectional view of the detail according to FIG. 19 according to line XXI-XXI, FIG. 22 shows a sectional view of the detail according to FIG. 19 according to line XXII-XXII, FIG. 23 shows an enlarged side view of the representation of detail VII according to FIG. 6 in a fourth alternative embodiment, FIG. 24 shows a sectional view of the detail according to FIG. 23 according to line XXIV-XXIV, FIG. 25 shows a sectional view of the detail according to FIG. 23 according to line XXV-XXV, and FIG. 26 shows a sectional view of the detail according to FIG. 25 according to line XXVI-XXVI.

The inhaler is used for administering a pulverulent medicament from a blister cavity which is arranged by the manufacturer on a bearing 3 which is dish-shaped in cross-section and is fixedly associated with a lower housing part 1 of a housing 2. The lower housing part 1 is provided with two opposing clip projections 4 which are arranged at free ends of locking arms 7 and are let into corresponding clip openings 5 in different planes of an upper housing part 6 in the form of a mouthpiece. The lower housing part 1 further has in its bottom 8 air inlet openings 9 through which, on inhalation, air flows from the surroundings into the inside of the housing 2. When the inhaler is in the delivery state, in which the blister cavity is accommodated unopened in the housing 2, the clip projections 4 engage in the clip openings 5 adjacent to the bottom of the lower housing part 1 and form first clip connections 10, piercing elements 11 for opening the blister cavity being at a distance from the blister cavity when the lower housing part 1 is in this position relative to the upper housing part 6. In order to open the blister cavity, the lower housing part 1 is displaced relative to the upper housing part 6, the clip projections 4 engaging in the slot-shaped clip openings 5 adjacent to the upper end of the upper housing part 6 and forming second clip connections. On account of the first clip connections 10 and the second clip connections, the user of the inhaler has both a visual and a tactile reminder of the condition of the blister cavity. In order to prevent the upper housing part 6 from being twisted relative to the lower housing part 1, they have an elliptical cross-section, the upper housing part 6 tapering in the direction towards its upper end in order to form an ergonomically advantageous contact surface for the lips of a user of the inhaler.

The piercing elements 11 have been punched out of a plate 12 of metal, at a distance from one another, and are bent at an acute angle relative to the plate 24 so that they point in the direction towards the bearing 3 for the blister cavity. In order to produce a relatively large opening in a cover film of the blister cavity while applying a comparatively small force, each piercing element has a triangular tip. The plate 12 is provided with centering holes 13 in which there engage centering pins 14 of a unit 15 for dispersing the pulverulent medicament, which centering pins 14 firmly hold the plate 12 after the application of pressure in the heated state. The plate 12 is so disposed that one piercing element 11 is arranged in the region of an inhalation channel 16 of the upper housing part 6 and one piercing element 11 is arranged laterally offset thereto. The unit 15, which is to be manufactured separately, is fixedly inserted in the inhalation channel 16 of the mouthpiece.

The medicament stored in the blister cavity, viewed in the direction of flow, upstream of the unit 15 for dispersing the pulverulent medicament passes on inhalation through a central bore 17 of the unit 15 into the mouthpiece inhalation channel 16, which widens in the direction towards an air outlet opening 18, the central bore 17 being located above the piercing element 11 associated with the inhalation channel 16 of the upper housing part 6.

Figure 7:
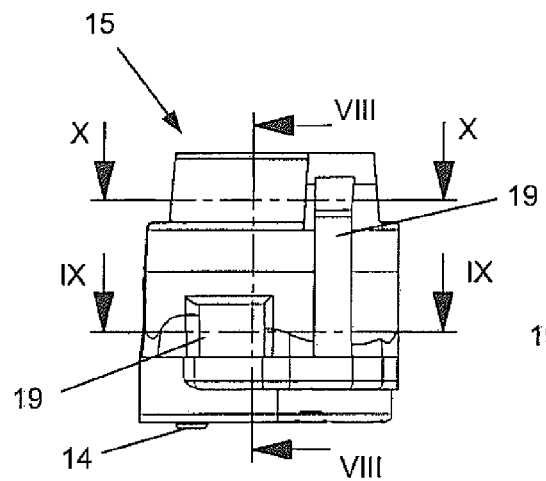
Figure 8:
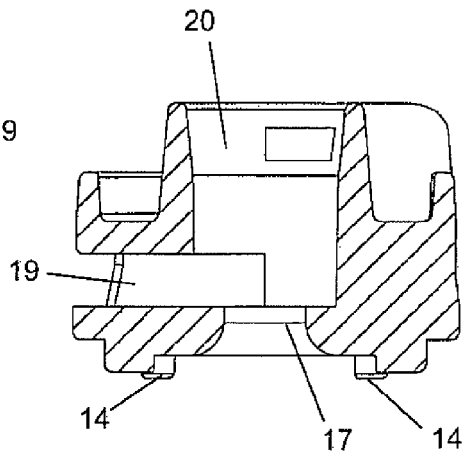
Figure 9:
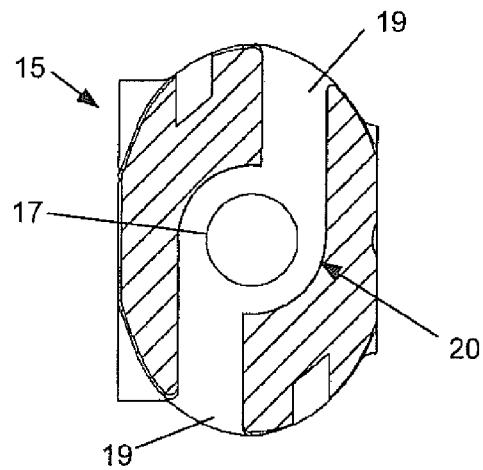
Figure 10:
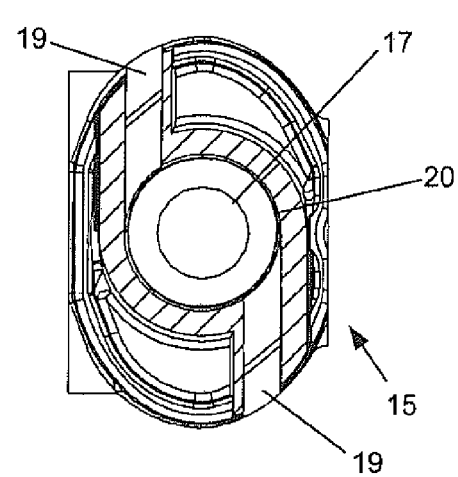

According to FIGS. 7 to 10, the unit 15 has on each side two inflow openings 19 for air from the surroundings, which inflow openings 19 are each arranged off-centre and are mutually offset and lead tangentially into a flow bore 20 which communicates with the inhalation channel 16 and represents almost an extension of the central bore 17. Owing to the arrangement of the inflow openings 19, a cyclone-like turbulent flow is produced in the flow bore 20 on aspiration; this turbulent flow, together with the air flowing through the central bore 17, which is loaded with the medicament, ensures that the powder particles of the medicament are finely distributed.

Figure 11:
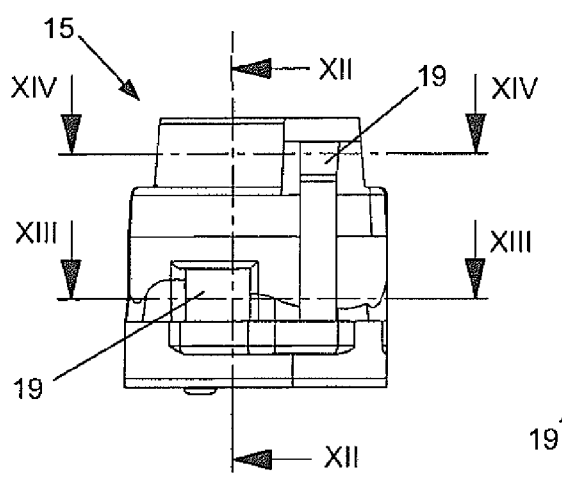
Figure 12:
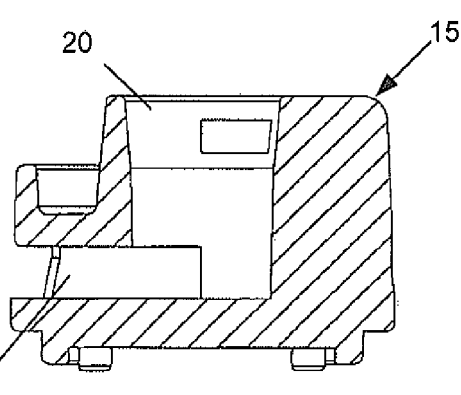
Figure 13:
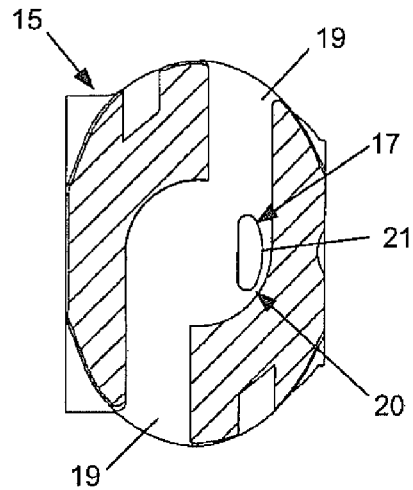
Figure 14:
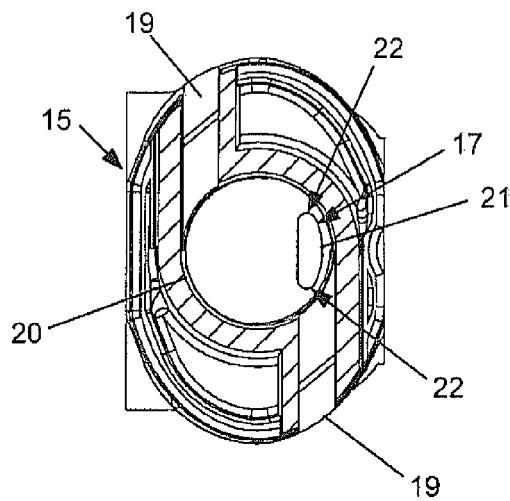

Also in the unit 15 according to FIGS. 11 to 14 there are provided on each side the two inflow openings 19 for air from the surroundings, which inflow openings are each arranged off-centre in the unit 15 and are mutually offset and lead tangentially into the flow bore 20 which communicates with the inhalation channel 16, the central bore 17 being in the form of a segment-shaped opening 21 with rounded corners 22.

Figure 15:
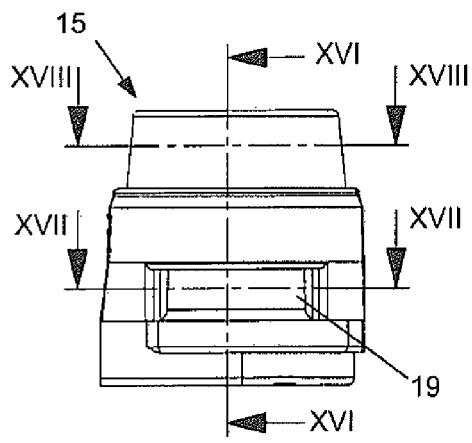
Figure 16:
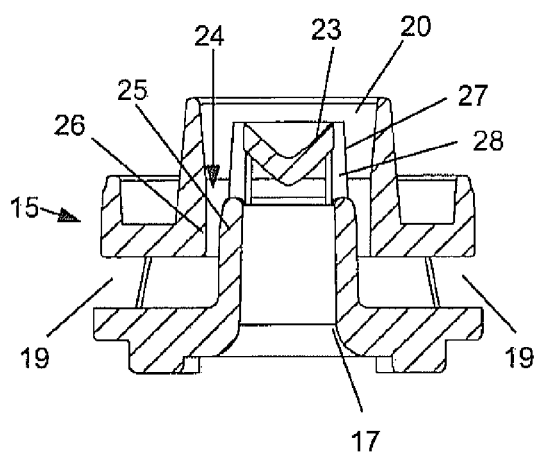
Figure 17:
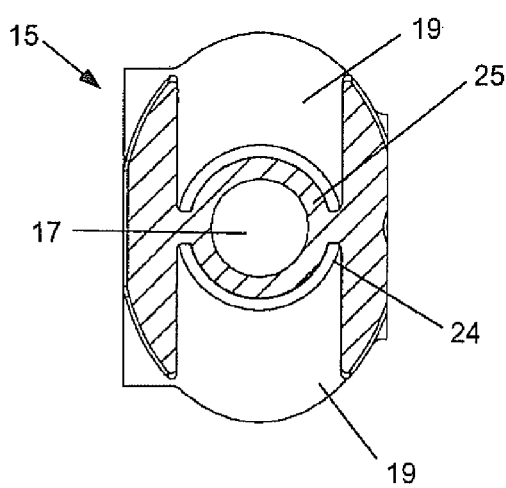
Figure 18:
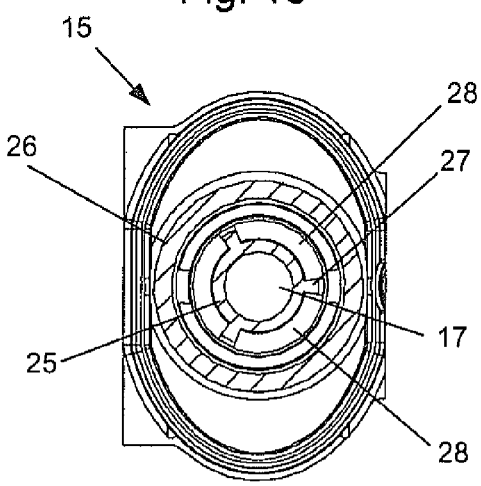

The unit 15 according to FIGS. 15 to 18 is equipped with a deflector plate 23 which extends conically above the central bore 17, coaxially in the flow bore 20, the tip 24 of the conical deflector plate 23 pointing in the direction towards the bearing 3 for the blister cavity containing the medicament and the deflector plate 23 having a smaller diameter than the flow bore 20 so that an annular space 24 having an inner wall 25 is formed between the central bore 17 and the flow bore 20, through which annular space 24 aspirated air flows, an outer wall 26 of the flow bore 20 overlapping the inner wall 25 of the annular space 24 and the deflector plate 23. The deflector plate 23 is connected to the inner wall 25 by webs 27, peripheral apertures 28 being formed for the flow connection of the central bore 17 to the flow bore 20. In order to create further turbulence in the air flow loaded with the medicament, the two inflow openings 19 are arranged diametrically oppositely in the unit 15 and have a width which is slightly greater than the diameter of the inner wall 25.

Figures 19, 20:
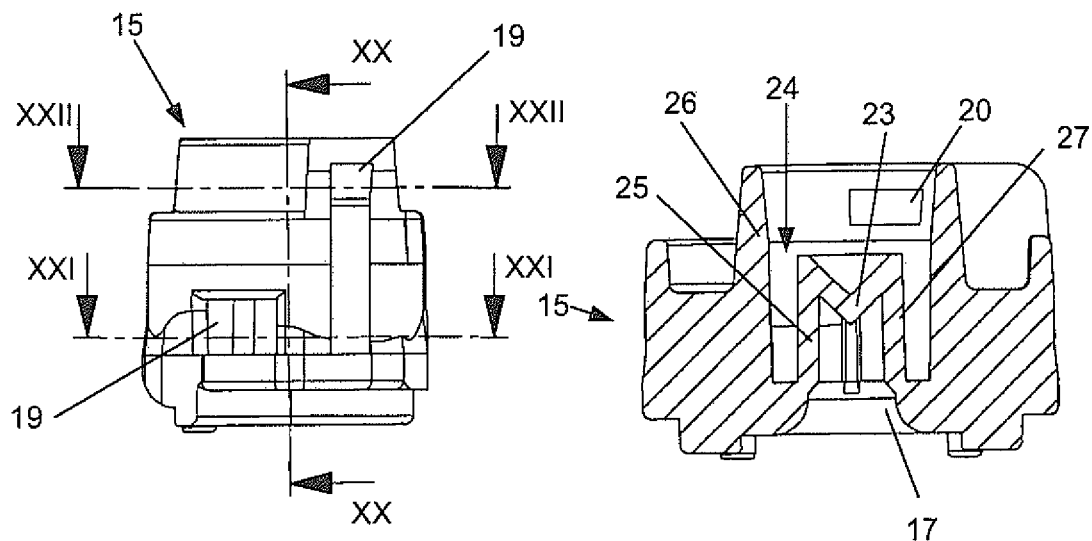
Figures 21, 22:
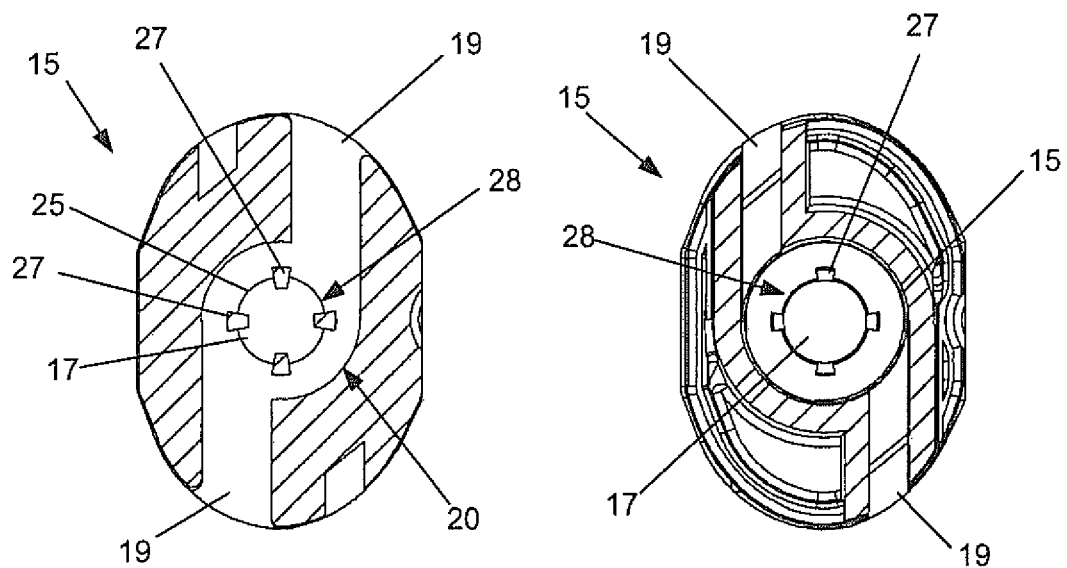

In the unit 15 according to FIGS. 19 to 22, the two inflow openings 19 for air from the surroundings, which are each arranged off-centre in the unit 15 and are also mutually offset, are let in on each side and lead tangentially first into the annular space 24 and then, perpendicularly thereto, into the flow bore 20. As explained hereinbefore, the deflector plate 23, which bridges the central bore 17, is conical in form and is disposed coaxially both to the central bore 17 and to the flow bore 20.

Figure 23:
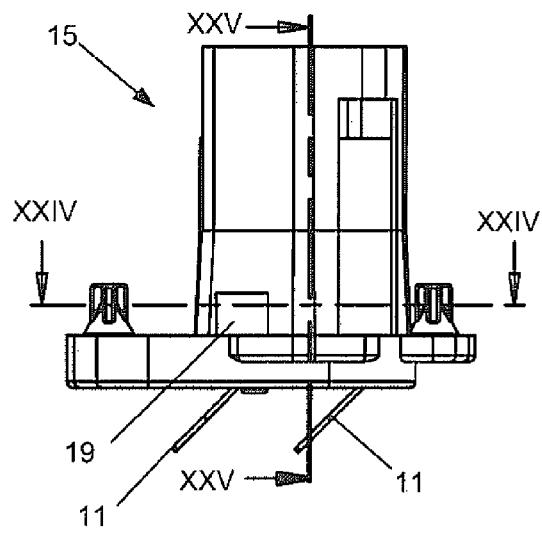
Figure 25:
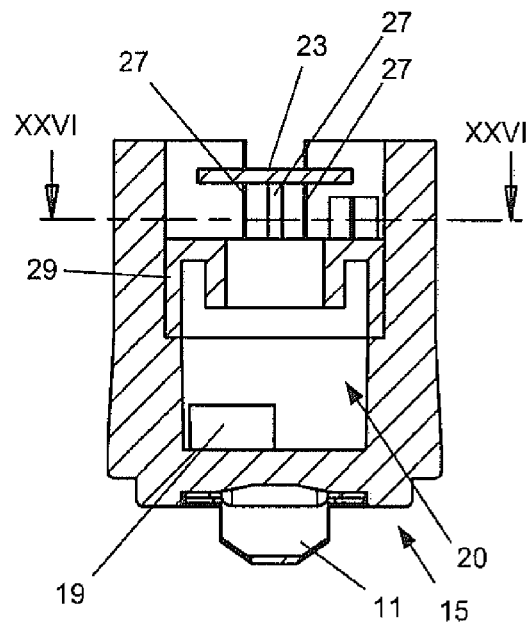
Figure 24:
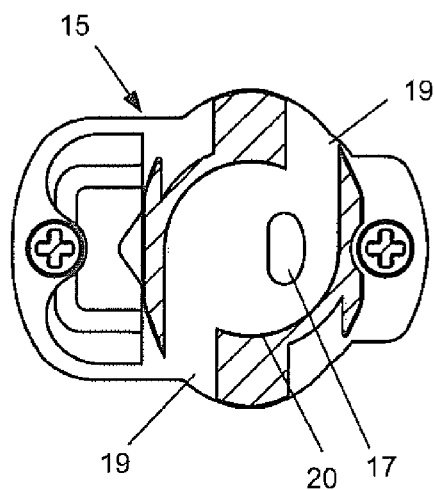
Figure 26:
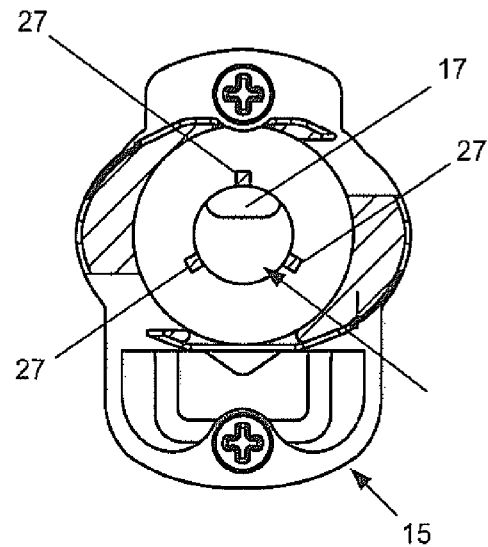

In the unit 15 according to FIGS. 23 to 26, the two inflow openings 19 for air from the surroundings, which are each arranged off-centre in the unit 15 and are also mutually offset, are let in on each side and lead tangentially into the flow bore 20 bridged by the deflector plate 23. The flat deflector plate 23 is connected via the webs 27 to a centering ring 29 inserted into the unit 15. The outside diameter of the deflector plate 23 is greater than the diameter of the flow bore 20 in the region of the centering ring 29.

A standard test was carried out to compare an inhalation device having a piercing element with an inhalation device having a piercing element and a deflector plate. A standard formulation containing BIBW 2948 was used as the test substance. The test served to study the release of the powder. The following results were found.

Dosage: 30 mg of the 25% test formulation (7.5 mg of active ingredient)

|  | Test | |
| --- | --- | --- |
|  | 1 | 2 |
| Inhalation device | Standard with piercing element without deflector plate | Standard with piercing element and with deflector plate |
| $FPD_{(4kPa)} < \mu m/mg$ (Vk/%) | 1.5 (23.7) | 1.9 (8.9) |
| $MMAD/\mu m$ (GSD) | 4.2 (1.9) | 3.9 (1.9) |
| $FPD_{(1kPa)}/FPD_{(4kPa)}$ | 0.27 | 0.56 |
| $FPF_{(4kPa)}/\%$ | 20.5 | 24.7 |

What is claimed is:

1. Inhaler for administration of a pulverulent medicament in the form of an inhalable substance, substance formulation or substance mixture from a blister cavity comprising a housing composed of an upper housing part in the form of a mouthpiece and having an inhalation channel, and a lower housing part, which has an air inlet opening, wherein the blister cavity is mounted in the lower housing part of the housing and is opened by piercing elements and wherein the upper housing part has a unit for dispersing the pulverulent medicament which is a separate piece that is fixedly secured in the inhalation channel of the mouthpiece, said unit having a central bore extending therethrough, the medicament being stored in a blister cavity receivable in the lower housing part upstream of the unit such that, on inhalation through the upper housing part, medicament is discharged from the blister cavity and the lower housing part and passes through the central bore of the unit in the upper housing part, wherein said unit is connected to the piercing elements and in that the unit comprises a flow bore that leads into the inhalation channel and at least one tangential inflow opening in communication with the flow bore, so that a cyclonic turbulent flow is produced in the flow bore prior to entry of the medicament into the inhalation channel, wherein in a first position the piercing elements are disposed at a distance from the blister cavity in a position locked by at least one first clip connection between the upper housing part and the lower housing part and, in a second position defined by at least one second clip connection, they project into the opened blister cavity.

2. Inhaler according to claim 1, wherein each piercing element has a triangular tip, one piercing element being arranged in the region of the inhalation channel and one piercing element being arranged offset laterally thereto.

3. Inhaler according to claim 1, wherein the piercing elements are made of a plastics material.

4. Inhaler according to claim 1, wherein the piercing elements and the unit for dispersion are one piece of material.

5. Inhaler according to claim 1, wherein the piercing elements are made of metal.

6. Inhaler according to claim 5, wherein the piercing elements project from a metal plate, wherein the plate and the piercing elements are made of a single plate of metal and the piercing elements are bent at an acute angle to the plate so that they point in the direction towards the blister cavity.

7. Inhaler according to claim 6, wherein the plate is connected in a positive-locking or friction-locked manner to the unit for dispersion.

8. Inhaler according to claim 1, wherein the lower housing part has two opposing clip projections, and corresponding clip openings are let into the upper housing part in different planes.

9. Inhaler according to claim 8, wherein the clip projections are arranged at free ends of opposing locking arms.

10. Inhaler according to claim 8, wherein one of the two clip openings is in a plane in which the blister cavity is opened and is in the form of a slot.

11. Inhaler according to claim 1, wherein the upper housing part is mounted to be displaceable relative to the lower housing part.

12. Inhaler according to claim 1, wherein that an anti-twist means is arranged between the upper housing part and the lower housing part.

13. Inhaler according to claim 1, wherein the upper housing part has a cylindrical or elliptical cross-section in which the lower housing part, which is cylindrical or elliptical in cross-section, is mounted and the upper housing part extends conically in the direction towards an air outlet opening, and the air inlet opening of the lower housing is located on a bottom of the lower housing part.

14. Inhaler according to claim 1, wherein the upper housing part and the lower housing part are each dish-shaped in cross-section, the lower housing part being mounted in the upper housing part.

15. Inhaler according to claim 1, wherein the blister cavity containing the pulverulent medicament is arranged in a bearing of the housing.

16. Inhaler according to claim 1, wherein the inhaler is provided with an air-tight outer packaging.

17. Inhaler according to claim 16, wherein the air-tight outer packaging is a film container.

18. Inhaler according to claim 1, wherein upon inhalation, air flows through an opening in the blister cavity and carries the medicament through the central bore of the unit into the inhalation channel of the mouthpiece, the unit having at least one radial inflow opening which communicates with the flow bore that leads into the inhalation channel.

19. Inhaler according to claim 18, wherein the central bore of the unit is disposed in alignment with one of the piercing elements.

20. Inhaler according to claim 18, wherein the central bore is surrounded by an annular space through which air flows and into which the inflow opening leads, the outer wall of the flow bore overlapping an inner wall of the annular space.

21. Inhaler according to claim 18, wherein two diametrally opposite inflow openings are provided, the width of which is slightly greater than the diameter of the inner wall.

22. Inhaler according to claim 18, wherein there are provided at least two mutually offset inflow openings which lead into flow channels on opposite sides of the unit which communicate with one another.

23. Inhaler according to claim 20, wherein the inner wall has axial apertures for the flow connection of the bore with the flow bore.

24. Inhaler according to claim 18, wherein the unit has in its flow bore a deflector plate for the medicament.

25. Inhaler according to claim 18, wherein the deflector plate is fastened to a centering ring inserted into the unit.

26. Inhaler according to claim 1, wherein it is for single use.

27. Inhaler for administration of a pulverulent medicament in the form of an inhalable substance, substance formulation or substance mixture from a blister cavity, comprising a housing composed of an upper housing part in the form of a mouthpiece and has an inhalation channel, and a lower housing part, said lower housing part having an air inlet opening, wherein said blister cavity is to be opened by piercing elements and is mounted in the lower housing part of the housing, wherein the inhalation channel of the upper housing part has a unit for dispersing the pulverulent medicament which is a separate piece that is fixedly secured in the inhalation channel of the mouthpiece, which unit is connected to the piercing elements, and wherein the medicament is stored in the blister cavity, upstream of the unit for dispersing the pulverulent medicament and passes through a central bore of the unit into the inhalation channel of the mouthpiece, the unit having at least one tangential inflow opening which communicates with a flow bore that leads into the inhalation channel wherein in a first position the piercing elements are disposed at a distance from the blister cavity in a position locked by at least one first clip connection between the upper housing part and the lower housing part and, in a second position defined by at least one second clip connection, they project into the opened blister cavity.

28. Inhaler according to claim 27, wherein each piercing element has a triangular tip, one piercing element being arranged in the region of the inhalation channel and one piercing element being arranged offset laterally thereto.

29. Inhaler according to claim 27, wherein the piercing elements are made of a plastics material.

30. Inhaler according to claim 27, wherein the piercing elements and the unit for dispersion are one piece of material.

31. Inhaler according to claim 27, wherein the piercing elements are made of metal.

32. Inhaler according to claim 31, wherein the piercing elements project from a metal plate, wherein the plate and the piercing elements are made of a single plate of metal and the piercing elements are bent at an acute angle to the plate so that they point in the direction towards the blister cavity.

33. Inhaler according to claim 32, wherein the plate is connected in a positive-locking or friction-locked manner to the unit for dispersion.

34. Inhaler according to claim 27, wherein the lower housing part has two opposing clip projections, and corresponding clip openings are let into the upper housing part in different planes.

35. Inhaler according to claim 34, wherein in that the clip projections are arranged at free ends of opposing locking arms.

36. Inhaler according to claim 34, wherein one of the two clip openings is in a plane in which the blister cavity is opened and is in the form of a slot.

37. Inhaler according to claim 27, wherein the upper housing part is mounted to be displaceable relative to the lower housing part.

38. Inhaler according to claim 27, wherein an anti-twist means is arranged between the upper housing part and the lower housing part.

39. Inhaler according to claim 27, wherein the upper housing part has a cylindrical or elliptical cross-section in which the lower housing part, which is cylindrical or elliptical in cross-section, is mounted and the upper housing part extends conically in the direction towards an air outlet opening, and the air inlet opening of the lower housing is located on a bottom of the lower housing part.

40. Inhaler according to claim 27, wherein the upper housing part and the lower housing part are each dish-shaped in cross-section, the lower housing part being mounted in the upper housing part.

41. Inhaler according to claim 27, wherein the blister cavity containing the pulverulent medicament is arranged in a bearing of the housing.

42. Inhaler according to claim 27, wherein the inhaler is provided with an air-tight outer packaging.

43. Inhaler according to claim 42, wherein the air-tight outer packaging is a film container.

44. Inhaler according to claim 27, wherein upon inhalation, air flows through an opening in blister cavity and carries the medicament through the central bore of the unit into the inhalation channel of the mouthpiece, the unit having at least one radial inflow opening which communicates with the flow bore that leads into the inhalation channel.

45. Inhaler according to claim 44, wherein the central bore of the unit is disposed in alignment with one of the piercing elements.

46. Inhaler according to claim 44, wherein the central bore is surrounded by an annular space through which air flows and into which the inflow opening leads, the outer wall of the flow bore overlapping an inner wall of the annular space.

47. Inhaler according to claim 44, wherein two diametrally opposite inflow openings are provided, the width of which is slightly greater than the diameter of the inner wall.

48. Inhaler according to claim 44, wherein there are provided at least two mutually offset inflow openings which lead into flow channels on opposite sides of the unit which communicate with one another.

49. Inhaler according to claim 46, wherein the inner wall has axial apertures for the flow connection of the bore with the flow bore.

50. Inhaler according to claim 44, wherein the unit has in its flow bore a deflector plate for the medicament.

51. Inhaler according to claim 44, wherein the deflector plate is fastened to a centering ring inserted into the unit.

52. Inhaler according to claim 27, wherein it is for single use.

* * * * *